(12) United States Patent
Hearn et al.

(10) Patent No.: US 10,589,041 B2
(45) Date of Patent: Mar. 17, 2020

(54) INHALER

(71) Applicant: Kind Consumer Limited, London (GB)

(72) Inventors: Alex Hearn, London (GB); Iain McDerment, Hertfordshire (GB)

(73) Assignee: KIND CONSUMER LIMITED, London (GB)

( * ) Notice: Subject to any disclaimer, the term of this patent is extended or adjusted under 35 U.S.C. 154(b) by 867 days.

(21) Appl. No.: 14/424,205

(22) PCT Filed: Aug. 27, 2013

(86) PCT No.: PCT/GB2013/052239
§ 371 (c)(1),
(2) Date: Feb. 26, 2015

(87) PCT Pub. No.: WO2014/033438
PCT Pub. Date: Mar. 6, 2014

(65) Prior Publication Data
US 2015/0217067 A1    Aug. 6, 2015

(30) Foreign Application Priority Data

Aug. 28, 2012  (GB) .................................. 1215278.1
Aug. 28, 2012  (GB) .................................. 1215282.3

(51) Int. Cl.
| | | |
|---|---|---|
| *A61M 15/00* | (2006.01) | |
| *A24F 47/00* | (2020.01) | |
| *A61M 15/06* | (2006.01) | |

(52) U.S. Cl.
CPC ....... *A61M 15/0091* (2013.01); *A24F 47/002* (2013.01); *A61M 15/002* (2014.02);
(Continued)

(58) Field of Classification Search
CPC . A61M 15/0086–0088; A61M 15/0091–0098; A61M 15/06;
(Continued)

(56) References Cited

U.S. PATENT DOCUMENTS

| | | | | |
|---|---|---|---|---|
| 3,456,646 A | * | 7/1969 | Phillips | A61M 15/0091 128/200.23 |
| 4,393,884 A | | 7/1983 | Jacobs | |
| 5,388,572 A | * | 2/1995 | Mulhauser | A61M 15/0045 128/203.15 |

FOREIGN PATENT DOCUMENTS

| | | |
|---|---|---|
| WO | 2010073018 A1 | 7/2010 |
| WO | 2011015825 A1 | 2/2011 |

(Continued)

OTHER PUBLICATIONS

International Search Report and Written Opinion dated Nov. 18, 2013 for Application No. PCT/GB2013/052239.
(Continued)

*Primary Examiner* — Samchuan C Yao
*Assistant Examiner* — Ned T Heffner
(74) *Attorney, Agent, or Firm* — Patterson + Sheridan, LLP

(57) ABSTRACT

An inhaler comprising a reservoir of an inhalable composition. A valve element moved by a flexible diaphragm and biased into a position in which it closes a composition flow path from a reservoir. A first air flow path is partly defined by one side of the diaphragm and a second air flow path is partly defined by the opposite side of the diaphragm. Each flow path has an outlet opening at an outlet end and the second flow path has an inlet upstream of the outlet end. The air flow paths are arranged such that suction at the outlet end causes a reduction in pressure in the first air flow path relative to the pressure in the second air flow path creating
(Continued)

Figure 1:
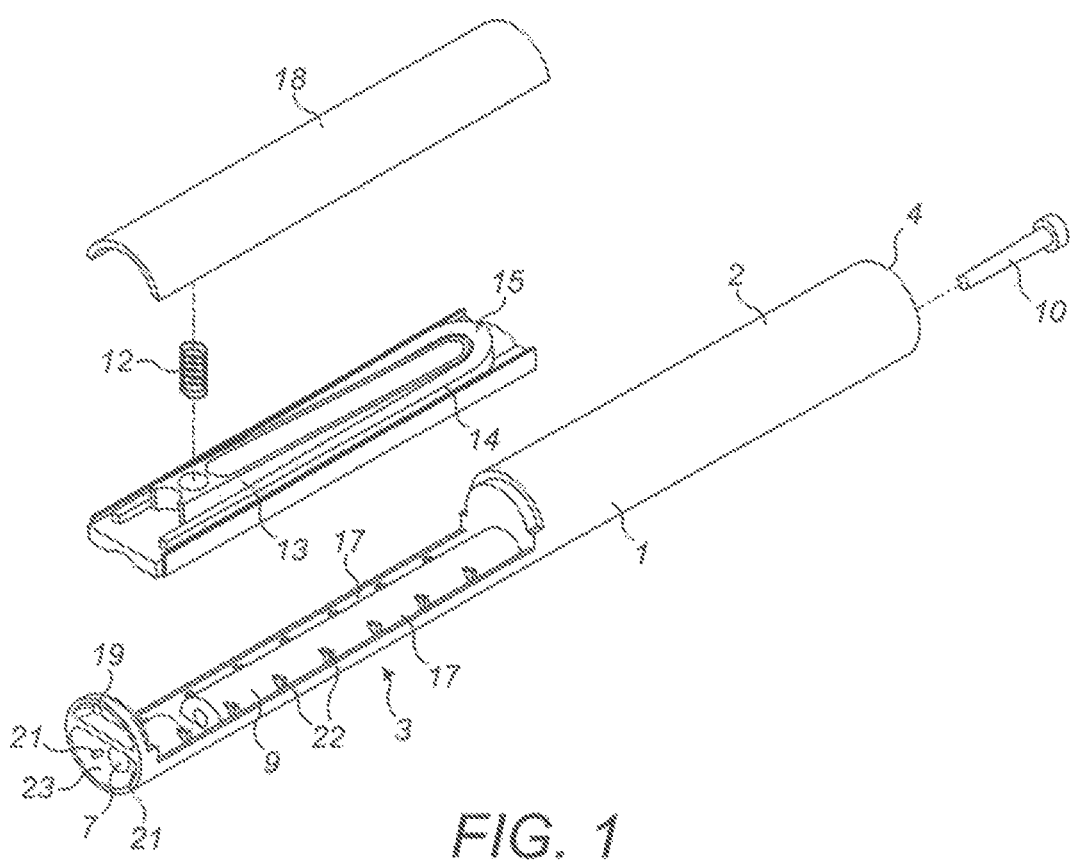
Figure 2:
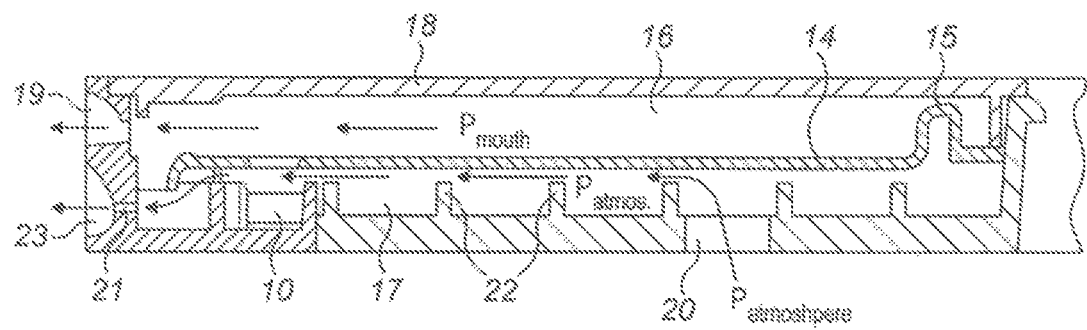
Figure 4:
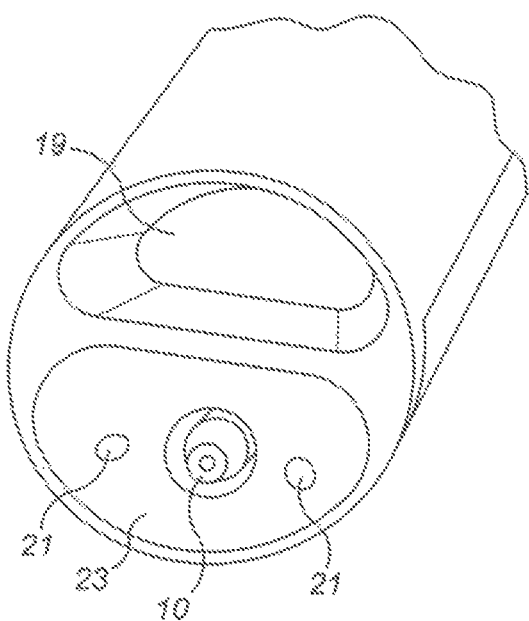
Figure 3:
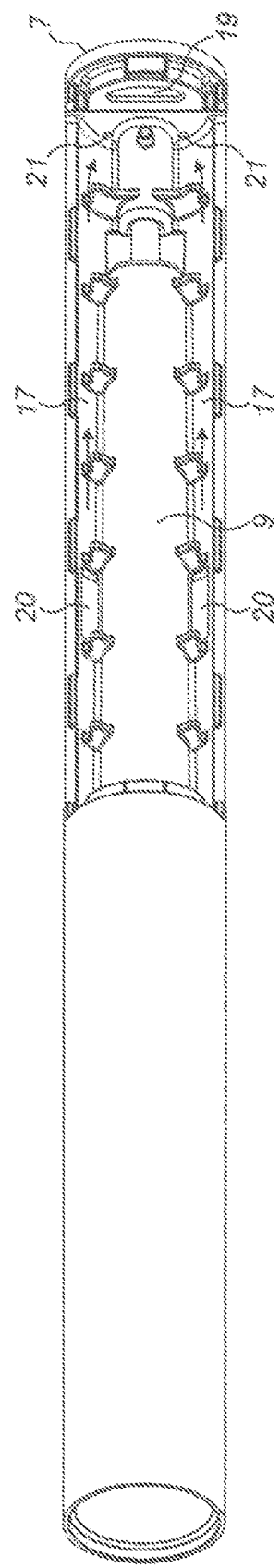
Figure 5:
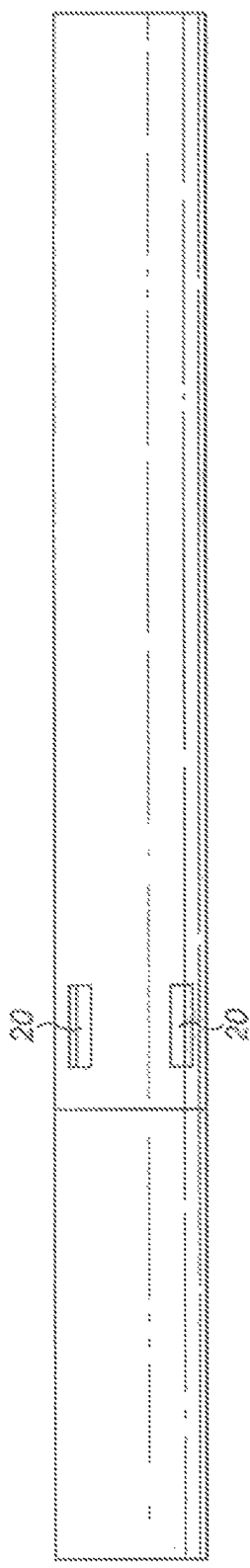
Figure 6:
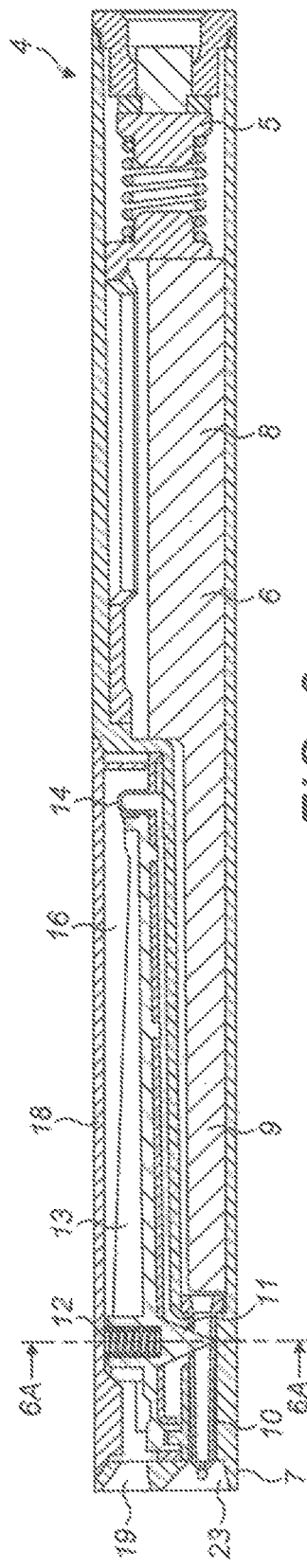
Figure 6A:
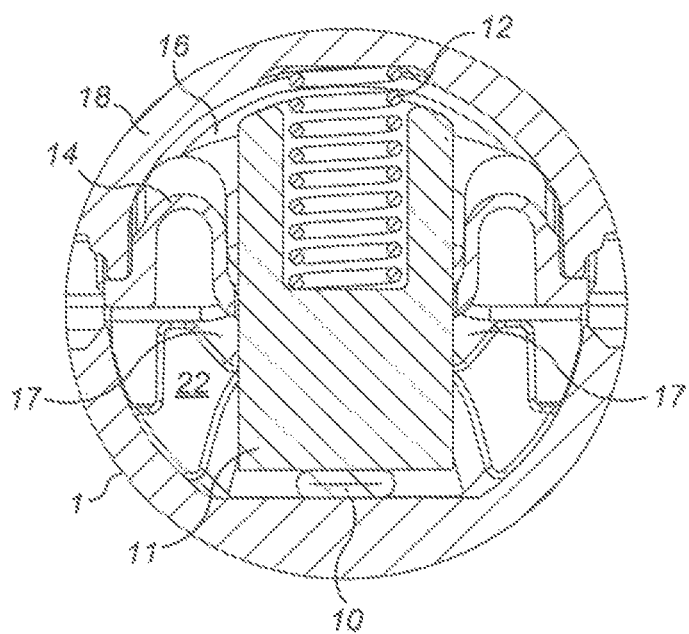

a pressure differential across the diaphragm that moves the valve element against the biasing force to open the composition flow path.

7 Claims, 5 Drawing Sheets

(52) U.S. Cl.
CPC ........ *A61M 15/0093* (2014.02); *A61M 15/06* (2013.01); *A61M 2209/045* (2013.01)

(58) Field of Classification Search
CPC ...... A61M 15/08–085; A61M 15/0056; A61M 15/006; A61M 15/0065; A61M 15/0068–0083; A61M 11/02; A61M 11/06; A61M 11/08; A24F 47/00; A24F 47/002; A24F 47/004; A24F 47/008
See application file for complete search history.

(56) References Cited

FOREIGN PATENT DOCUMENTS

| WO | 2011015826 A1 | 2/2011 |
| WO | WO2011015825 A1 * | 2/2011 |
| WO | 2011107737 | 9/2011 |

OTHER PUBLICATIONS

United Kingdom Search Report dated Dec. 4, 2012 for Application No. GB1215278.1.

* cited by examiner

INHALER

The present invention relates to an inhaler, specifically a breath-operated device.

A number of embodiments of breath-operated devices are known in the art, Furthermore, there are a select number that include a means of using inhalation energy and pressure exertion to create an actuation trigger. For example U.S. Pat. No. 6,581,590 discloses an actuator mechanism formed by a suction tube which communication the mouthpiece with a diaphragm member and provides air to the user. This works on a single air flow and operates a latching mechanism, where air enters the device as the canister actuator slides away from the diaphragm member. Additionally U.S. Pat. No. 6,318,366 provides a supply valve and diaphragm for a pneumatically operated gas demand apparatus. Furthermore WO2006/079751 discloses a trigger mechanism that releases medications for inhalation which can deliver liquid formulation in a bolus.

These devices operate an on/off configuration whereby the prescribed breath-activation system delivers a set bolus on triggering at a given flow rate and will then switch off once the bolus has been emitted.

WO 2011/015826 discloses an inhaler which is specifically designed for use as a simulated cigarette and nicotine delivery system as well fast-acting medicines and pharmaceutical agents. This is provided with a breath-activated valve comprising a deformable tube which is pinched closed by a valve element carried on a vane. This vane is biased closed by a spring. The vane is surrounded by a flexible diaphragm. An air flow path is defined above the flexible diaphragm. This has air inlet orifices which let air into the air flow path above the diaphragm part way along the simulated cigarette. This air then flows along the top of the diaphragm before exiting at an outlet opening at the end of the simulated cigarette which, in use, is sucked on by a user. As the inlet is smaller than the outlet, this suction reduces the pressure in the space above the diaphragm. This causes the vane and hence the valve element to be lifted against the action of the spring thereby opening the composition flow path to allow the composition to exit the simulated cigarette for inhalation.

This vane system is highly effective as a compact breath-operated valve specifically for the use in an inhaler. However, this has now been improved to provide enhanced operation.

One important aspect in designing a simulated cigarette is to make the experience of using the simulated cigarette as close as possible to the real smoking experience. When a user sucks on a cigarette, they use a considerably lower inhaled flow rate as compared, for example, to the suction required to open an inhaler primarily designed for medicinal purposes, such as an asthma inhaler. This can be in the range of 1 L/m compared to a dry powder inhaler that may need as high as 60 L/m flow rate for lung deposition.

It is desirable to have a breath-operated valve which is opened at a suction force which is as close as possible to the suction force by the user smoking a cigarette. In practice, it is desirable to acheive a triggering of the valve at the lowest possible inhalation flow rate to ensure a consistent sensation of draw during the inhalation cycle. With higher trigger points, greater suction is required and this leads to a more binary mode of mechanism and an 'on/off' aspect of valve triggering. This must also be done within the confines of the space available inside an inhaler that is the same size as a cigarette.

According to the present invention, there is provided:
an inhaler comprising a reservoir of an inhalable composition;
a housing containing the reservoir and having an outlet end;
a composition flow path for the flow of the composition from the reservoir and out of a composition outlet at the outlet end of the housing;
a valve element biased by a biasing force into a position in which it closes the composition flow path;
a flexible diaphragm arranged to move the valve element; and
a first air flow path partly defined by one side of the diaphragm, and a second air flow path partly defined by the opposite side of the diaphragm, each flow path having an outlet opening at the outlet end and the second flow path having an inlet upstream of the outlet end, wherein the air flow paths are arranged such that suction at the outlet end causes a reduction in pressure in the first air flow path relative to the pressure in the second air flow path creating a pressure differential across the diaphragm that moves the diaphragm and hence moves the valve element against the biasing force to open the composition flow path.

Thus, the present invention provides two low paths which are arranged so that the pressures change on opposite sides of the diaphragm is enhanced when suction is applied. The sensitivity of the breath-operated valve is considerably enhanced compared to WO 2011/015826 in which there is only a single air flow path across the top of the diaphragm. Beneath the diaphragm in WO 2011/015826, the only outlet is the composition outlet. Therefore, as the diaphragm moves up, the space beneath it expands causing a pressure drop. This effectively acts as a brake on the opening of the valve. By having the second flow path, there is no fixed volume of gas to expand, thereby removing the brake and enhancing the sensitivity of the valve. The mechanism can be sensitised to the user's breath, calibrating the energy of the inhalation to the amount of formulation delivered, thereby creating a device that a user can control and thus self-tritrate formulation over multiple doses with ease.

Preferably, the pressure in the second air flow path remaining substantially at atmospheric when suction is applied to the outlet ends.

Preferably, the second air flow path is configured so that there is no increase in pressure in the second air flow path when suction is applied at the outlet end.

The open area in the second flow path at its upstream end is preferably larger than its open area at the outlet end. This will cause the pressure in the second flow path to increase when suction is applied by generating a higher pressure drop across the opening at the outlet end.

The first flow path may have an opening at its upstream end that is smaller than the opening at the outlet end. However, preferably, the first flow path is a blind flow path which is closed other than the opening at the outlet end. Thus, suction at the outlet end will effectively simply draw air out of the first air flow path.

The composition flow path may be arranged on the same side of the diaphragm as the first air flow path. In this case, the valve element would effectively have to "reach around" the composition flow path and biased back towards the composition flow path. Preferably, the composition flow path is on the same side of the diaphragm as the second flow path. This provides for a simpler construction of the valve element.

While the inhaler has been specifically designed to be a simulated cigarette, it has broader applications as an inhaler, for example, to dispense medicament, particularly in a situation where a low trigger force is required. This is especially advantageous when delivering medications or vaccines which require rapid delivery and greater compliance compared with traditional inhalers, for example β2-adrenergic agonists, classes of opioids including synthetic and semi-synthetic, hormones or neuro-transmitters and not limited to anticholinergics, corticosteroids, cannabinoids, PDE4-inhibitors, LTD4-antagonists, EGFR-inhibitors, dopamine agonists, antihistamines, PAF-antagonists and PI3-kinase inhibitors or LTD4-antagonists antivirals, antibiotics, antigens or therapeutic proteins.

An example of an inhaler in accordance with the present invention will now be described with reference to the accompanying drawings, in which FIG. 1 is an exploded perspective view of an inhaler;

FIG. 2 is a schematic axial cross-section through the outlet end of the inhaler in the plane containing an air flow path and with the vane removed for clarity;

FIG. 3 is a perspective view of the outlet end of the inhaler with the cover, vane and diaphragm removed to show the air flow paths;

FIG. 4 is a perspective view of the outlet end of the inhaler;

FIG. 5 is a plan view of the inhaler;

FIG. 6 is a full cross-section of the inhaler; and

FIG. 6A is a cross-section through line 6A-6A in FIG. 6.

The present invention relates to an improvement of the outlet valve for an inhaler such as that disclosed in WO 2011/015826. For further details of the device and its refill mechanism, reference is made to WO 2009/001078.

As shown in FIG. 1, the device comprises a housing 1 which is broadly divided into two parts. The distal part is a reservoir 2 and the proximal part is the breath-activated valve mechanism 3. At the distal end 4 is a refill valve 5 allowing the reservoir to be filled. The reservoir may contain a wick 6 as disclosed in PCT/GB2011/000285. At the opposite end is the outlet end 5 which will be described in more detail below.

As best shown in FIG. 6, the reservoir has a portion 8 adjacent to the distal end 4 which occupies substantially the entire cross-section of the inhaler at this point. A second portion 9 which is closer to the outlet end 7 occupies a relatively small portion of the cross-section of the inhaler because, as shown in FIG. 6, this part of the inhaler also accommodates the valve mechanism described below and provides space for the air flow paths also described below.

As can be seen from FIGS. 1 and 3, this second portion 9 of the reservoir is part of the same molding as the housing 1 and runs along the lower part of the inhaler.

An elastomeric insert 10 in the form of a tube open at both ends is inserted from the distal end, but forms an outlet flow path at the proximal end of the inlet path as shown in FIG. 6. This insert 10 is normally pinched closed by a valve element 11 which is biased downwardly by a spring 11. This pinch closed valve mechanism is described in greater detail in WO 2011/015825.

The valve element 11 is part of a vane 13 which extends along most of the outlet end of the inhaler. The vane 13 is surrounded by a diaphragm 14 which extends across the entire lower face of the vane 13, with the exception of the orifice through which the valve element 11 projects. This valve element is sealed around its periphery to the surrounding housing. At the distal end of the diaphragm 14 is a kink 15 which provides some degree of freedom for the vane 13 to move up and down. The opposite end of the vane 13 is integral with a surrounding frame that is filled into the housing such that there is a direct connection between the frame and vane to provide a hinge about which the vane pivots.

A mechanism for opening the valve element il against the action of the spring 12 will now be described.

This is achieved by first 16 and second 17 air flow paths. The first flow path 16 is above the diaphragm 14 with the top of the flow path being formed by housing part 18 which is fixed to the housing 1 once the valve elements are in place. The first air flow path is essentially provided by a first air flow path outlet orifice 19 which leads into the space occupied by the vane 13 above the diaphragm 14. This flow path has no other orifices.

The second air flow path 17 is below the diaphragm 14 and is defined by a pair of second air flow path inlet orifices 20 (only one of which is shown in FIG. 2). In the present example, the second air flow path is actually defined by two separate paths which extend from the inlet orifices 20 along passages 17 which are defined by the housing 1 on the lower surface and the diaphragm 11 at its upper surface and which extends alongside the second portion 9 of the reservoir to the outlet end terminating at a pair of second air flow path outlet orifices 21 which are smaller than the corresponding inlet orifices 20. The flow through the second air flow path is depicted by arrows in the lower part of FIG. 2 and in FIG. 3. Baffles 22 are provided along the second air flow path 17 to increase the follow resistance in this path.

As a user sucks on the outlet end 7, air is sucked out of the first flow path outlet orifice 15 thereby lowering the pressure in the first air flow path 16. At the same time, air is drawn in through the second flow path air inlet orifices 20. The combination of a reduced pressure above the vane and the prevention of a significant pressure reduction below the vane causes the vane to be moved upwardly deforming the diaphragm and raising the valve element against the action of the spring 12. When a user stops sucking on the outlet end, the pressure above and below the diaphragm equalises and the spring 12 returns the valve element 11 to a position in which it pinches the insert 10 closed.

The invention claimed is:

1. An inhaler comprising;

a reservoir of an inhalable composition;

a housing containing the reservoir and having an outlet end;

a composition flow path for the flow of the composition from the reservoir and out of a composition outlet at the outlet end of the housing;

a valve element biased by a biasing force into a first position in which it closes the composition flow path;

a flexible diaphragm arranged to move the valve element; and a first air flow path partly defined by one side of the diaphragm, a second air flow path partly defined by the opposite side of the diaphragm, each flow path having an outlet opening at the outlet end and the second flow path having an inlet upstream of the outlet end, wherein the air flow paths are separate from the composition flow path and are arranged such that suction at the outlet end causes a reduction in pressure in the first air flow path relative to the pressure in the second air flow path creating a pressure differential across the diaphragm that moves the diaphragm and hence moves the valve element against the biasing force to a second position in which the composition flow path is open, and wherein:

cessation of the suction at the outlet end equalizes the pressure differential across the diaphragm, causing the biasing force is configured to return the valve element to the first position in which it closes the composition flow path, the composition flows from the reservoir and out of the composition outlet as long as the suction is continuously applied at the outlet end, and cessation of the suction at the outlet end causes the composition to stop flowing from the reservoir when a user stops sucking on the outlet end of the inhaler.

2. An inhaler as claimed in claim 1, wherein the pressure in the second air flow path remaining substantially at atmospheric when suction is applied to the outlet ends.

3. An inhaler as claimed in claim 1, wherein the second air flow path is configured so that there is no increase in pressure in the second air flow path when suction is applied at the outlet end.

4. An inhaler according to claim 1, wherein the open area of the second air flow path at its inlet is larger than its open area at the outlet end.

5. An inhaler according to claim 1, wherein the first air flow path is closed other than the opening at the outlet end.

6. An inhaler according to claim 1, wherein the composition flow path is on the same side of the diaphragm as the second flow path.

7. An inhaler according to claim 1, wherein baffles are provided in the second air flow path to increase the flow resistance therethrough.

* * * * *